United States Patent [19]
Matsunaga et al.

[11] Patent Number: 4,584,886
[45] Date of Patent: Apr. 29, 1986

[54] RESOLUTION DEVICE FOR SEMICONDUCTOR THIN FILMS

[75] Inventors: Hideki Matsunaga, Yokohama; Naoyuki Hirate, Yokosuka; Akira Okada, Tokyo, all of Japan

[73] Assignee: Kabushiki Kaisha Toshiba, Kawasaki, Japan

[21] Appl. No.: 654,216

[22] Filed: Sep. 25, 1984

[30] Foreign Application Priority Data

Sep. 26, 1983 [JP] Japan ............................. 58-176503

[51] Int. Cl.$^4$ ............................................. G01N 1/28
[52] U.S. Cl. ............................... 73/863; 73/863.21; 356/36; 422/299
[58] Field of Search ............... 73/863, 863.21, 864.91; 422/298, 299; 356/36, 37

[56] References Cited

U.S. PATENT DOCUMENTS

| | | | |
|---|---|---|---|
| 3,824,016 | 7/1974 | Woodriff et al. | 356/36 X |
| 3,976,377 | 8/1976 | Wu et al. | 356/36 |
| 4,361,401 | 11/1982 | Smith, Jr. et al. | 356/36 |

FOREIGN PATENT DOCUMENTS

| | | | |
|---|---|---|---|
| 110894 | 8/1979 | Japan | 356/36 |
| 2982 | 1/1980 | Japan | 356/36 |
| 60807 | 5/1980 | Japan | 356/36 |
| 90838 | 7/1980 | Japan | 73/863 |
| 14736 | 1/1982 | Japan | 73/863 |
| 204432 | 12/1982 | Japan | 73/863 |

OTHER PUBLICATIONS

"Layerwise Atomic-Absorption Analysis of Semiconductor Films with Sampling by Ion Etching", *Industrial Laboratory;* vol. 41, No. 6, pp. 843-845; 12-1975; B. I. Kuzovkin et al.

"Determination of Platinum and Palladium in Blood and Urine by Flameless Atomic Absorption Spectrophotometry"; *Analytical Chemistry;* vol. 48, No. 11, pp. 1472-1474; Sep. 1976; A. H. Jones.

Mitchell, J. W., "Teflon Apparatus for Vapor Phase Destruction of Silicate Materials", Analytical Chemistry, vol. 46, No. 2, p. 326, Feb. 1974.

*Primary Examiner*—Stewart J. Levy
*Assistant Examiner*—Tom Noland
*Attorney, Agent, or Firm*—Schwartz, Jeffery, Schwaab, Mack, Blumenthal & Evans

[57] ABSTRACT

The resolution device for semiconductor films according to the present invention comprises a sealed container, a storage container installed in the sealed container for storing hydrofluoric acid to generate hydrogen fluoride gas, a semiconductor film supporter installed in the sealed container, and a receptacle of resolved solution installed at the bottom of the sealed container for receiving the resolved solution of the semiconductor films. The semiconductor films held by the film supporter are resolved by hydrogen fluoride gas which is generated from the storage container of hydrofluoric acid and has a low impurity content. The resolved solution is collected in the receptacle for resolved solution, and is supplied directly to the flameless atomic absorption spectrophotometer.

7 Claims, 2 Drawing Figures

RESOLUTION DEVICE FOR SEMICONDUCTOR THIN FILMS

BACKGROUND OF THE INVENTION

1. Field of the Invention

The present invention relates to a resolution device for semiconductor thin films, more particularly, to a semiconductor thin film resolution device for preparing samples, that are scarcely contaminated by the decomposition reagents or the surrounds, to be used in analyzing ultratrace amounts of impurities in semiconductor thin films.

2. Description of the Prior Art

Semiconductor films such as $SiO_2$ film or $Si_3N_4$ film have been used as a partial diffusion masking for doping reagents or a protective film for sputtered metallic films in silicon semiconductors. When there are contained in the film impurities like Na, K, or Fe, the electrical characteristics of the semiconductor are affected significantly even if the amount may be extremely minute. For this reason, it is necessary to suppress the amount of these impurities to the lowest level possible in order to enhance the capabilities of the semiconductors such as in a Giant Scale Integration. To accomplish such a goal, it is necessary to be able to measure accurately the concentration of impurities in semiconductor films.

For measuring impurities in semiconductor films, the flameless atomic absorption spectrophotometer has been used in the past. Measurements are taken by placing the semiconductor film samples for flameless atomic absorption spectrophotometry on the flameless atomic absorption spectrophotometer. However, there exists a serious problem in the preparation of samples for spectrophotometry.

Namely, according to the prior art method of preparing samples, a semiconductor film is soaked in a mixture of hydrofluoric acid and sulfuric acid, and after direct decomposition, the dissolved solution obtained is evaporated and dried to obtain the residues. Samples for flameless atomic absorption spectroanalysis are obtained by diluting the residues to a predetermined volume with pure water. However, in this prior art method, contamination by the reagent used for resolving the semiconductor sample is exceedingly large. For example, even when reagents refined by the sub-boiling distillation method or the ion exchange method are used, these reagents already contain impurities (Na, K, and the like) in excess of 0.1 ppb so that it has been extremely difficult to accurately measure the amount of impurities in a semiconductor film of less than $10^{-10}$ g/cm$^2$ by means of flameless atomic absorption spectrophotometry.

SUMMARY OF THE INVENTION

An object of the present invention is to provide a semiconductor film resolution device which is capable of preparing semiconductor film samples for flameless atomic absorption spectrophotometry that are scarcely contaminated by the resolution reagents or by the surroundings.

The other object of the present invention is to provide a semiconductor film resolution device which is capable of preparing semiconductor film samples of which the flameless atomic absorption spectrophotometer can measure the impurity amount with high sensitivity.

Still another object of the present invention is to provide a resolution device which is capable of preparing semiconductor film samples simply.

Briefly described, these and other objects of the present invention are accomplished by the provision of an improved semiconductor film resolution device which includes a sealed container, a container installed within the sealed container for storing hydrofluoric acid to be used for generating hydrogen, fluoride gas, means installed within the sealed container holding semiconductor films, and a receptacle installed at the bottom of the sealed container for receiving the resolved solution of the semiconductor films. In the above construction, the semiconductor films that are held by the holding means are resolved by hydrogen fluoride gas with a low impurity content generated at the storage container of the hydrofluoric acid. The resolved solution is collected in the receptacle for the resolved solution, and is supplied directly to a flameless atomic absorption spectrophotometer.

BRIEF DESCRIPTION OF THE DEVICE

These and other objects, features, and advantages of the present invention will be more apparent from the following description of a preferred embodiment, taken in conjunction with the accompanying drawings, in which:

FIG. 1 is a simplified cross-section view of an embodiment of the resolution device for semiconductor films in accordance with the present invention; and FIG. 2 is a graph illustrating the rate of resolution for various kinds of semiconductor films by hydrogen fluoride gas, by a resolution device in accordance with the present invention.

DESCRIPTION OF THE PREFERRED EMBODIMENTS

Figure 1:
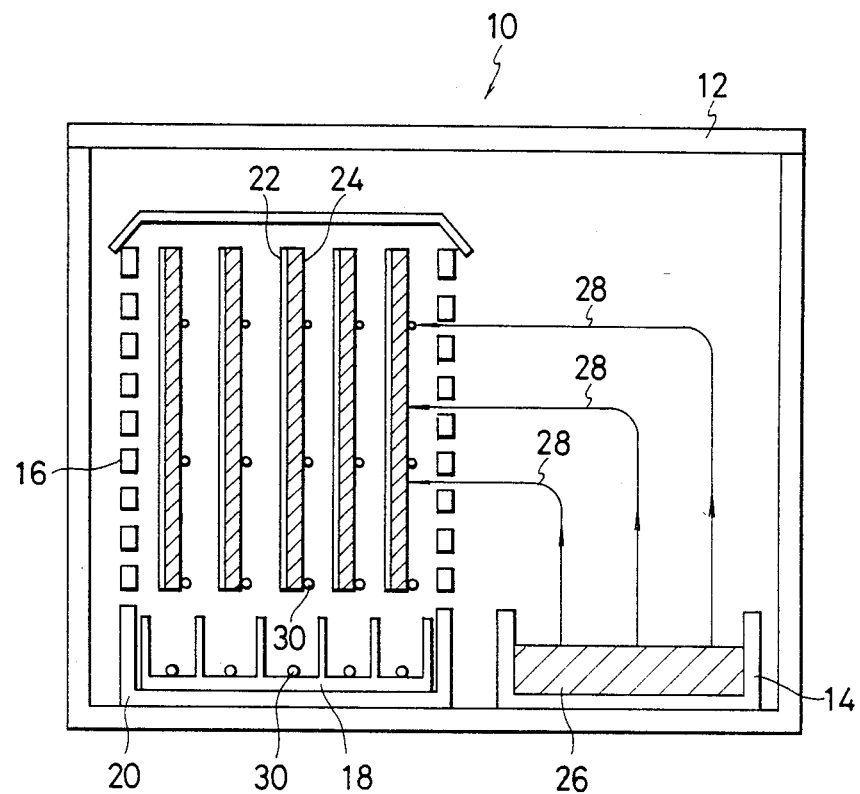

Referring to FIG. 1, there is shown a resolution device for semiconductor films embodying the present invention with the reference numeral 10. This semiconductor film resolution device includes a sealed container 12, a hydrofluoric acid storage container 14, such as a beaker for evaporating hydrogen fluoride gas, a film supporter 16 such as a wafer carrier, and a resolved solution receptacle 18, a receiving tray which is positioned to receive the resolved solution drops from the semiconductor film or films. The wafer carrier 16, together with a carrier holding stand 20, forms a means for holding films. The material for all parts of the device is Teflon ® (polytetrafluoroethylene manufactured by E.I. duPont de Nemours and Co., Wilmington DL), and the device is cleaned by heating in mixed solution of hydrofluoric acid, nitric acid, and hydrochloric acid and is washed away with pure water prior to its use.

Next, the operation of the resolution device will be described.

Figure 2:
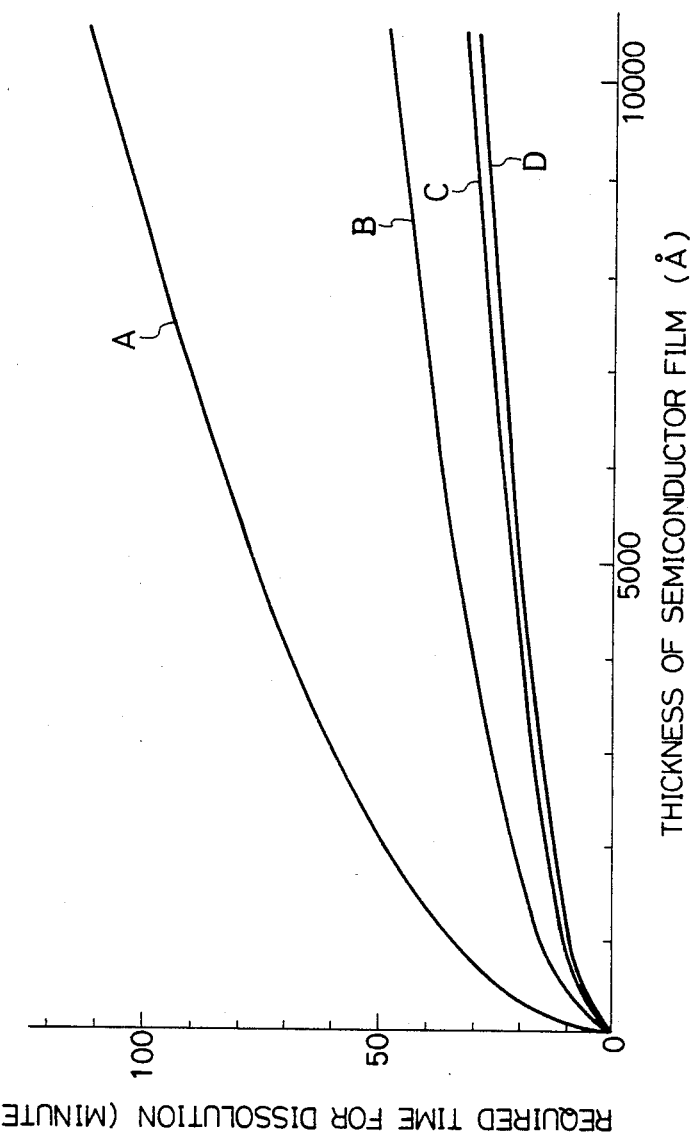

The sample wafers 22 with $SiO_2$ or $Si_3N_4$ films 24 are leaned against the wafer carrier 16, hydrofluoric acid 26 is poured into the evaporation beaker 14, and the entire device is left standing for a predetermined duration of time. Little effect has been observed in the sensitivity and accuracy of analysis even when the device has been left standing for 300 minutes after the completion of resolution. The temperature at which it is desirable to be left at is to be in the range of 20° to 35° C. Semiconductor films 24 are resolved completely by the hydrogen fluoride gas 28 that is generated from the beaker 14, and most of the resolved solution drops 30 into the resolved solution receptacle 18. Here, the rate of resolution varied with the type and thickness of the film 24. The time required for resolution in the case of 100 ml of hydrofluoric acid (50%), temperature of 30° C., spatial volume of the sealed container of about 16,000 cm$^3$, and film thickness of 10,000 Å, as shown in FIG. 2, are 31 minutes for thermally oxidized SiO$_2$ films C, 29 minutes for LPCVD-SiO$_2$ films D, 47 minutes for plasma CVD-Si$_3$N$_4$ films B, and 108 minutes for LPCVD-Si$_3$N$_4$ films A, respectively. The resolved solution is collected with a micropipette, and following stirring and weighing, is measured directly with a flameless atomic absorption spectrophotometer without carrying out separate concentration by evaporation and drying.

Since the resolution treatment according to the present method is carried out with hydrogen fluoride gas without directly acid-resolving the semiconductor films with resolution solution, it becomes possible to achieve detection with an extremely high sensitivity. The impurity content of the hydrogen fluoride gas used in the present device is extremely low, since it is the gas that has evaporated out from the hydrofluoric acid solution, even if the solution contains a certain amount of impurities. Therefore, the impurity content of the solution collected for samples is correspondingly low also. If evaporation is done by heating the hydrofluoric acid solution, then the impurities in the solution tend also to evaporate out, giving rise to a possibility of increasing the impurity content of the hydrogen fluoride gas. This is the reason why it is desirable to have evaporation at the room temperature in the range of 20° C. and 35° C.

EXAMPLES OF THE INVENTION

Here, we will further explain the present invention with reference to some examples. The resolution treatment according to the present invention was carried out in the following ways.

EXAMPLE 1

The impurities in the SiO$_2$ films (232 Å thick) prepared on Si wafers by thermal oxidation, was resolved by means of the device in accordance with the present invention to be examined with the flameless atomic absorption spectrophotometer.

The conditions for resolution and measurement were as follows.

(1) Conditions for resolution of films . . . hydrofluoric acid (50%): 100 ml, temperature: 30° C., spatial volume of the sealed container: approximately 16,000 cm$^3$, and the time left standing for resolution: 60 minutes.

(2) Measurement conditions for flameless atomic absorption spectrophotometry . . . drying: 30 seconds at 120° C., ashing: 30 seconds at a predetermined temperature (For Na: 600° C., K: 700° C., and Fe and Cr: 1,000° C.), atomization: 8 seconds at a predetermined temperature (For Na: 2,500° C., K: 2,700° C., and Fe and Cr: 2,800° C.), carrier gas: argon at 100 ml/min, but 0 ml/min during atomization, wavelength of measurement: 589.0 nm for Na, 766.5 nm for K, 248.3 nm for Fe, and 359.4 nm for Cr, light source for correcting the interference absorption: used halogen-tungsten lamp for analysis of Na and K, and deuterium lamp for analysis of Fe and Cr.

Under the conditions described in the foregoing, it was possible to analyze $4\times10^{-12}$ g/cm$^2$ for Na, $1\times10^{-12}$ g/cm$^2$ for K, $2.7\times10^{-11}$ g/cm$^2$ for Fe, and $5\times10^{-13}$ g/cm$^2$ for Cr. In contrast, with the prior art method of combined direct acid resolution—flameless atomic absorption spectrophotometry; (1) Conditions for resolution of films . . . resolved films in 10 minutes at 30° C. with mixed acid solution of 5 ml of hydrofluoric acid (50%), 0.1 ml of sulfuric acid (96%), and 5 ml of pure water. After evaporating and drying the decomposed solution for 2 hours at about 160° C., it was diluted with 5 ml of pure water. (2) Measurement conditions for flameless atomic absorption spectrophotometry . . . same as the conditions described earlier; it was not possible to detect Na, K, and Fe of less than $2\times10^{-10}$ g/cm$^2$ and Cr of less than $1\times10^{-10}$ g/cm$^2$, due to impurities in the reagents used.

EXAMPLE 2

By resolving impurities in SiO$_2$ films (3000 Å thick) prepared on Si wafers by the LPCVD method, by means of the resolution device according to the present invention, and by examining the samples with the flameless atomic absorption spectrophotometer; (1) Resolution conditions for films . . . 100 ml of hydrofluoric acid (50%), at temperature of 30° C., about 16,000 cm$^3$ of spatial volume of the sealed container, and 120 minutes of time for resolution and leaving as it is. (2) Measurement conditions for flameless atomic absorption spectrophotometry . . . same as the conditions in example 1., it was possible to analyze $3.3\times10^{-11}$ g/cm$^2$ for Na, $2.2\times10^{-11}$ g/cm$^2$ for K, $7.8\times10^{-10}$ g/cm$^2$ for Fe, and $3.4\times10^{-12}$ g/cm$^2$ for Cr. By the prior art method (same conditions as for the existing method given in example 1), however, it was not possible to detect Na, K, and Cr, except for Fe: $8\times10^{-10}$ g/cm$^2$.

EXAMPLE 3

By resolving impurities in Si$_3$N$_4$ films (10000 Å thick) prepared on Si wafers by the plasma CVD method by means of the resolution device according to the present invention, and by examining the samples by the flameless atomic absorption spectrophotometer (same conditions as in example 2), it was possible to analyze $1.7\times10^{-11}$ g/cm$^2$ for Na, $2.0\times10^{-12}$ g/cm$^2$ for K, $5.5\times10^{-10}$ g/cm$^2$ for Fe, and $8.2\times10^{-11}$ g/cm$^2$ for Cr. By the prior art method (same conditions for the existing method as those given in example 1), however, it was not possible to detect Na, K, and Cr, except for Fe: $6\times10^{-10}$ g/cm$^2$.

In summary, in the resolution device according to the present invention, samples are decomposed with hydrogen fluoride gas of high purity, rather than directly acid resolving it, so that it is possible to reduce the contamination to a substantial degree. In addition, due to the circumstances that there is no operation of evaporation and dying, and that the resolution is carried out inside a sealed container, it is also possible to reduce the contamination from the surroundings. From the above, with the device according to the present invention, it becomes possible to accomplish a super-high sensitivity which is 1,000 times as high as for the prior art method, and to analyze metallic impurities, such as Na, K, Fe, and others, of the order of $10^{-13}$ g/cm$^2$ in the films. Moreover, the operation for preparation of resolved solutions to be used as samples for analysis is simple such that the industrial significance of the present invention is quite substantial.

Furthermore, the storage container of hydrofluoric acid which is a part of the device according to the present invention, may be of any make as long as it is capable of storing a predetermined amount of hydrofluoric acid, and of evaporating and generating from it hydrogen fluoride gas efficiency. Also, the means for holding the semiconductor films is a unit which is installed within the sealed container to hold or support the edges of the semiconductor films to be decomposed, having such a positional relationship as to have the semiconductor films resolved by making contact with the hydrogen fluoride gas that comes from the storage container. The holding means may be made in such a way as to hold just one film sample (for example, a sample wafer with an attached film) or may be made in such a way as to hold a plurality of film samples. It should be noted that what is meant here by "holding" includes the concept of fixing to something as well as the action of merely resting against something. In order to hold and simultaneously resolve a plurality of film samples, it is desirable to install partitions which separate each samples. Correspondingly, it is also desirable to have partitions in the receptacle for the decomposed solution so as to receive the resolved solution for each of the plurality of film samples.

The material of the components which constitute the device of the present invention, may be any material as long as it does not interfere, either directly or indirectly, with precise measurements of impurities in the films to be measured. However, in view of the fact that the gas to be used for resolution is hydrogen fluoride, it is desirable to use Teflon ®. Teflon ®, not only has excellent acid-proof and heat-proof properties but also permits an easy removal of impurities by washing with a mixed solution of hydrofluoric acid, nitric acid, hydrochloric acid, and the like. The dissolution of impurities from teflon which have undergone such a washing is extremely small so that it is considered to be a material which is suitable for the objects of the present invention.

Various modifications will become possible for those skilled in the art after receiving the teachings of the present disclosure without departing from the scope thereof.

What is claimed is:

1. A semiconductor film resolution device for manufacturing samples to be used for analyzing ultratrace amounts of impurities in semiconductor films by resolving the films with a resolution reagent gas in a sealed container, comprising:
    (a) storage means in said sealed container for storing hydrofluoric acid and for generating hydrogen fluoride gas;
    (b) hydrofluoric acid stored in said storage means so as to generate said hydrogen fluoride gas;
    (c) means for holding at least one semiconductor film sample within said sealed container so as to contact said sample with said hydrogen fluoride gas; and
    (d) resolved solution tray means provided in said sealed container for receiving resolved solution from said sample so as to separate said resolved solution from both said sample and said hydrofluoric acid.

2. A semiconductor film resolution device as claimed in claim 1, wherein said container, said storage means, said means for holding said semiconductor film sample, and said resolved solution tray means are all comprised of polytetrafluoroethylene.

3. A semiconductor film resolution device as claimed in claim 1, wherein said resolved solution tray means comprises a tray divided by partitions into a plurality of solution-receiving receptacles, said tray being arranged in said sealed container such that each solution-receiving receptacle of said plurality receives resolved solution from a predetermined film sample.

4. A semiconductor film resolution device as claimed in claim 1, wherein said storage means comprises means for storing hydrofluoric acid and for generating hydrogen fluoride gas at about room temperature, such that said hydrofluoric acid stored in said storage means is evaporated at a temperature range between about 20° and 35° C.

5. A semiconductor film resolution device as claimed in claim 4, wherein said storage means for storing hydrofluoric acid consists essentially of an open storage container provided within said sealed container.

6. A semiconductor film resolution device as claimed in claim 5, wherein said device does not comprise means for heating said hydrofluoric acid.

7. A semiconductor film resolution device as claimed in claim 1, wherein said storage means comprises a storage container, said means for holding said film sample comprises a carrier holding stand, and said resolved solution tray means comprises a resolved solution receiving tray, said solution receiving tray being placed on said carrier holding stand below said film sample and said storage container being placed beside said carrier holding stand in said sealed container, such that (a) said hydrogen fluoride gas can pass from said storage container to said carrier holding stand and into contact with said film sample and (b) resolved solution can separate from said film sample and be received in said receiving tray.

* * * * *